(12) United States Patent
Holub et al.

(10) Patent No.: US 12,051,506 B2
(45) Date of Patent: Jul. 30, 2024

(54) RECOMMENDATION PRIORITIZATION AND TASK THROTTLING

(71) Applicant: Clover Health, Jersey City, NJ (US)

(72) Inventors: Kevin Holub, San Francisco, CA (US); Christopher James Lauinger, Golden, CO (US); Melanie Goetz, Oakland, CA (US)

(73) Assignee: Clover Health, Jersey City, NJ (US)

( * ) Notice: Subject to any disclaimer, the term of this patent is extended or adjusted under 35 U.S.C. 154(b) by 877 days.

(21) Appl. No.: 16/842,052

(22) Filed: Apr. 7, 2020

(65) Prior Publication Data

US 2021/0313061 A1 Oct. 7, 2021

(51) Int. Cl.
| | | |
|---|---|---|
| G16H 50/20 | (2018.01) | |
| G16H 10/20 | (2018.01) | |
| G16H 10/60 | (2018.01) | |
| G16H 40/40 | (2018.01) | |
| G16H 40/67 | (2018.01) | |
| G16H 80/00 | (2018.01) | |

(52) U.S. Cl.
CPC ............. *G16H 50/20* (2018.01); *G16H 10/20* (2018.01); *G16H 10/60* (2018.01); *G16H 40/40* (2018.01); *G16H 40/67* (2018.01); *G16H 80/00* (2018.01)

(58) Field of Classification Search
None
See application file for complete search history.

(56) References Cited

U.S. PATENT DOCUMENTS

| | | | |
|---|---|---|---|
| 7,447,643 B1 | 11/2008 | Olson et al. | |
| 2005/0131740 A1* | 6/2005 | Massenzio | G06Q 10/10 705/2 |
| 2007/0260741 A1* | 11/2007 | Bezancon | H04L 67/52 707/E17.11 |
| 2013/0332214 A1* | 12/2013 | George | G16H 40/20 705/7.15 |
| 2014/0136230 A1* | 5/2014 | Berdia | G16H 50/20 705/2 |
| 2014/0278678 A1* | 9/2014 | Malkin | G06Q 10/06316 705/7.19 |
| 2017/0053088 A1 | 2/2017 | Walker et al. | |
| 2018/0182475 A1* | 6/2018 | Cossler | G16H 50/50 |

(Continued)

OTHER PUBLICATIONS

Office Action for U.S. Appl. No. 16/842,010, dated Feb. 17, 2023, Holub, "Recommendation Prioritization and Task Throttling", 23 Pages.

(Continued)

*Primary Examiner* — Devin C Hein

(74) *Attorney, Agent, or Firm* — Lee & Hayes, P.C.; Mike Merkelbach

(57) ABSTRACT

Systems and methods including analyzing profiles, generating medical recommendations, prioritizing the medical recommendations, throttling the medical recommendations, and transmitting a prioritized set of medical recommendations to a device that displays the information are disclosed. The medical recommendations may be prioritized based on an importance of the recommendation to a patient, a medical severity, and/or prior interaction with the system. The medical recommendations may be throttled to determine a number of recommendations to display to a medical provider during a period of time, such as a patient examination.

20 Claims, 7 Drawing Sheets

(56) References Cited

U.S. PATENT DOCUMENTS

2019/0035496 A1    1/2019   Netzer et al.
2019/0096526 A1    3/2019   Hirsch et al.
2019/0355472 A1   11/2019   Kutzko
2021/0313060 A1   10/2021   Holub et al.

OTHER PUBLICATIONS

Office Action for U.S. Appl. No. 16/842,010, dated Sep. 25, 2023, Holub, "Recommendation Prioritization and Task Throttling", 26 pages.

* cited by examiner

```
                                                          ← 500
```

GENERATE MEDICAL RECOMMENDATIONS ASSOCIATED WITH A PATIENT, INDIVIDUAL ONES OF THE MEDICAL RECOMMENDATIONS INCLUDING AT LEAST ONE OF A POTENTIAL DIAGNOSIS, A GAP IN MEDICAL COVERAGE, OR A MEDICATION RECOMMENDATION, THE MEDICAL RECOMMENDATIONS ASSOCIATED WITH A RANKING BASED AT LEAST IN PART ON FIRST DATA INDICATING FIRST HISTORICAL USE, BY A MEDICAL SERVICE PROVIDER, OF AN APPLICATION CONFIGURED TO PRESENT THE MEDICAL RECOMMENDATIONS AND SECOND DATA INDICATING SECOND HISTORICAL USE OF THE APPLICATION IN ASSOCIATION WITH THE PATIENT
502

↓

RECEIVE THIRD DATA INDICATING A SCHEDULE ASSOCIATED WITH THE MEDICAL SERVICE PROVIDER, THE SCHEDULE INCLUDING APPOINTMENTS INCLUDING A FIRST APPOINTMENT ASSOCIATED WITH THE PATIENT, THE FIRST APPOINTMENT INDICATING A DURATION OF TIME SCHEDULED FOR THE FIRST APPOINTMENT
504

↓

DETERMINE A SET OF THE MEDICAL RECOMMENDATIONS TO PRESENT ON A USER INTERFACE DURING THE FIRST APPOINTMENT BASED AT LEAST IN PART ON THE FIRST DATA, THE THIRD DATA, AND THE RANKING
506

↓

GENERATE A USER INTERFACE INCLUDING THE SET OF THE MEDICAL RECOMMENDATIONS, THE USER INTERFACE CAUSING DISPLAY OF THE SET OF THE MEDICAL RECOMMENDATIONS DURING THE FIRST APPOINTMENT
508

FIG. 5

RECOMMENDATION PRIORITIZATION AND TASK THROTTLING

BACKGROUND

Doctors, nurses, or other medical professionals often examine patients to determine health related issues. Examination(s) may include visits in-person (e.g., hospital or in-home), over the phone, and/or virtually. During an examination, medical professionals may be provided information associated with the patient. Determining what information to present to a medical professional during an examination, for instance, may be important in properly diagnosing a patient and/or identifying future measures to take. Described herein are improvements in technology and solutions to technical problems that may be used, among other things, to more efficiently utilize time of patient examinations.

BRIEF DESCRIPTION OF THE DRAWINGS

The detailed description is set forth below with reference to the accompanying figures. In the figures, the left-most digit(s) of a reference number identifies the figure in which the reference number first appears. The use of the same reference numbers in different figures indicates similar or identical items. The systems depicted in the accompanying figures are not to scale and components within the figures may be depicted not to scale with each other.

FIG. 5 illustrates a flow diagram of an example method for the remote computing resource(s) of FIG. 1 to prioritize and determine a set of medical recommendations to display during a patient examination.

DETAILED DESCRIPTION

Figure 1:
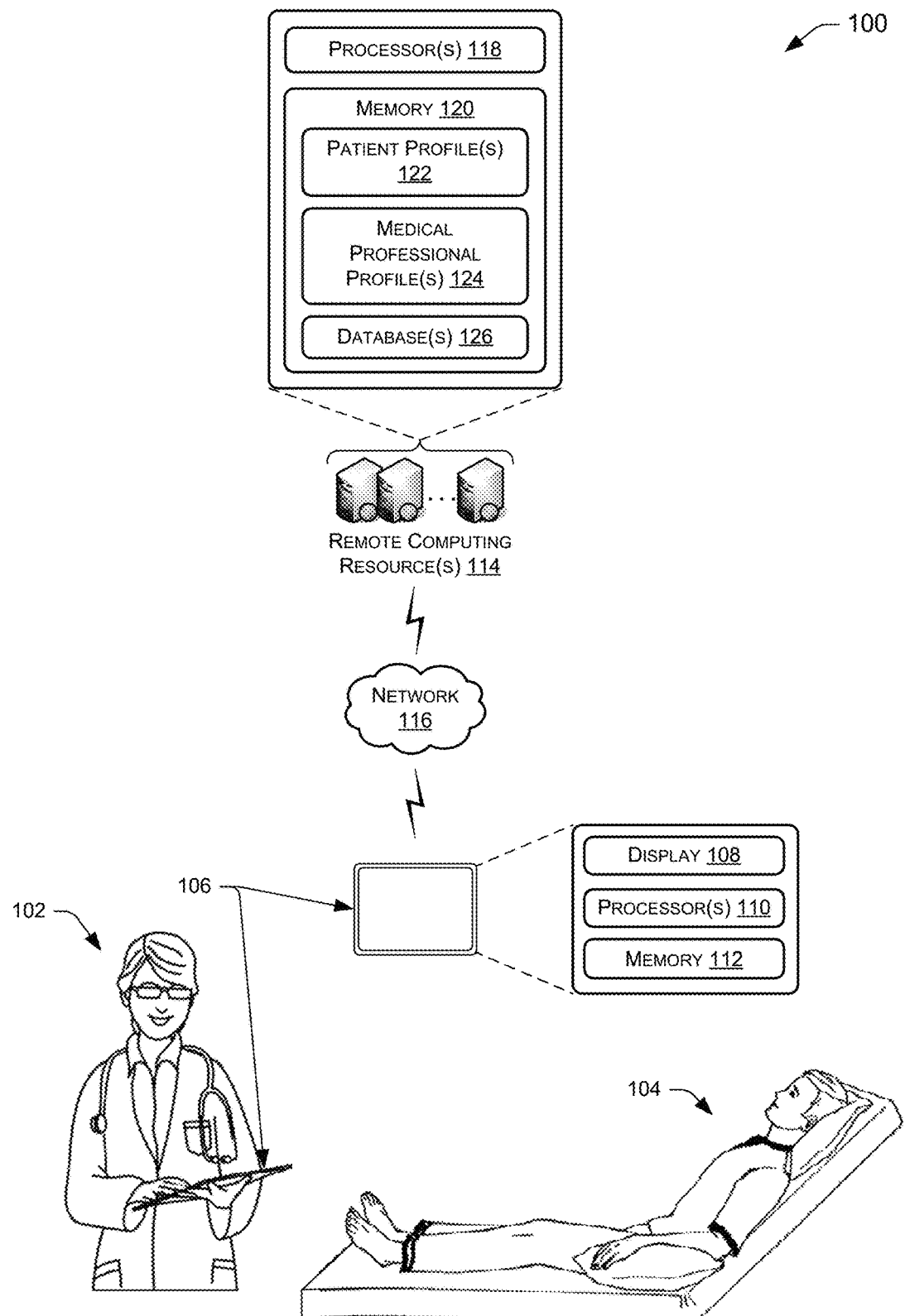
FIG. 1 illustrates an example diagram of prioritizing medical recommendations in a patient examination environment.

Systems and methods for dynamically prioritizing medical recommendations (e.g., potential diagnosis, gap in medical coverage, medication recommendation, etc.) and throttling tasks associated with the medical recommendations to display to a medical professional are described herein. A medical professional may have a number of medical examinations scheduled throughout the day with numerous patients each requiring specialized care. During a medical examination, a medical professional may utilize a list of tasks corresponding to medical recommendation(s) associated with the patient to complete during the examination. However, given the number of medical examinations the medical professional has scheduled on a given day, the amount of time spent during each medical examination may be very brief, for example, 15 minutes. Thus, the number of tasks that a medical professional can complete during a patient examination may be limited. The number of tasks a medical professional is able to complete may depend on a number of variables. For example, some medical professionals may complete tasks in a more efficient manner than other medical professionals. This may depend on the severity associated with the tasks, a number of variables associated with a patient (age, gender, previous medical history, etc.), and/or the amount of experience of the medical professional. When tasks associated with medical recommendation(s) are not prioritized properly, a medical professional may not have enough time during a patient examination to complete or even view the medical recommendation. As a result, a potentially crucial screening for the patient may not be brought to the attention of a medical professional during the limited examination.

This disclosure provides techniques for prioritizing medical recommendation(s) (e.g., a potential diagnosis, potential gaps-in-coverage, a medication recommendation, etc.) and presenting a viable number of the medical recommendation(s) that a medical professional will be able to complete during a patient examination. The recommendation(s) may be provided to a device operated by the medical professional, such as a tablet, computer, or phone, and the device may be configured to display the recommendation(s). The recommendation(s), for example, may include at least one of a potential diagnosis, a medication recommendation, or a gap in medical coverage, or something of the like. The device may present the recommendation(s) in a number of ways. For example, the recommendation(s) may be presented in a manner such that the recommendation(s) are categorized based on whether the recommendation(s) correspond to the potential diagnosis, the medication recommendation, or the gap in medical coverage. Additionally, or alternatively, the recommendation(s) may be represented by task(s) presented on the device operated by the medical professional, the tasks corresponding to the recommendation(s). The device may be configured to present an optimal number of recommendation(s) to the medical professional depending on a number of variables, such as, but not limited to, historical data representing an average number of recommendation(s) a medical professional completes during patient visits and/or an average number of recommendation(s) other medical professionals complete during visits associated with the patient. The device may be configured to receive input. The input may be associated with the recommendation(s), such as, for example, accepting or rejecting a recommendation associated with a potential diagnosis. In some examples, the input may be stored in association with a medical professional profile maintained by a remote computing resource(s) (e.g., cloud, server, etc.). The input may include an indication as to why a recommendation was accepted or rejected. The remote computing resource(s) may determine a priority of the recommendation(s), and/or a number of recommendation(s) to send to the device and display to the medical professional.

The recommendation(s) displayed on the device may be received from and/or generated by the remote computing resource(s). In some examples, the recommendation(s) may be tailored according to the patient's medical history, symptoms, and/or personal information associated with the patient. For example, the remote computing resource(s) may include a database to various types of data. In some examples, the remote computing resource(s) may store patient profiles corresponding to patients. Additionally, or alternatively, the remote computing resource(s) store medical records, news, diagnostics, statistics, and/or other medical information. Additionally, or alternatively, the remote computing resource(s) may also to store medical professional profiles corresponding to medical professionals and/or medical records, news, diagnostics, statistics, and/or other medical information associated with previous appointments involving the medical professional. The remote computing resource(s) may analyze the patient profiles, such as, for example, a medical history of the patient, to determine recommendation(s), or task(s), to present to the medical professional. Additionally, or alternatively, the remote computing resource(s) may analyze the medical professional profile, such as, for example, a historical record of utilized information, to determine a number of the recommendation(s), or task(s), to present to the medical professional. In some examples, a recommendation may be associated with one or more suspected diagnoses of a patient, a medication recommendation for the patient, and/or a gap in medical coverage recommendation for the patient. Additionally, or alternatively, the recommendation(s) may be associated with corresponding justifications, such as, for example, one or more test results, medical history, personal information, and/or identifying information associated with test results (e.g., a name of a company performing the test). In some examples, the recommendation(s) may be presented to a medical professional in a limited manner, providing for a prioritized list of tasks for the medical professional to complete during the limited patient appointment.

The remote computing resource(s) may employ one or more machine learning algorithms or models to generate the recommendation(s). In some instances, the machine learning models may correlate a patient's medical history or historical trends with one or more recommendations of the patient, despite, in some instances, the patient's medical history, and/or any other additional information accessible by the remote computing resource(s), failing to indicate the potential diagnosis. More specifically, while a patient's medical history may include symptoms associated with an illness, these symptoms, individually, may not be correlated to a potential disease. In some examples, the machine learning models then function to aggregate and analyze trends in a patient's medical history as well as, for example, trends in another patient's medical history, to determine one or more potential diagnoses, medication recommendations, potential gaps-in-coverage, and/or other medical recommendation(s).

In some examples, the recommendation(s) may include a potential diagnosis. The potential diagnosis may be a potential disease that the remote computing resource(s) has determined the patient may have based on the one or more machine learning models. For example, the potential diagnosis may include chronic heart disease, chronic kidney disease, vascular disease, diabetes, obesity, congestive heart failure, etc. The one or more machine learning models may consider numerous factors associated with a patient to determine a potential diagnosis, such as, for example, medications the patient takes, age of the patient, lab results associated with the patient, etc. These factors, that are utilized to determine a potential diagnosis, may be included with the recommendation as a justification for the recommendation.

Additionally, or alternatively, the recommendation(s) may include a medication recommendation. The medication recommendation may be a recommendation that a patient should begin taking a new medication. Additionally, or alternatively, the medication recommendation may be, for example, a recommendation that a patient switch from a 30-day fill of a prescribed medication to a 90-day fill of the prescribed medication. The one or more machine learning models may consider numerous factors associated with a patient to determine a medication recommendation, such as, for example, medications the patient takes, age of the patient, lab results associated with the patient, etc. These factors, that are utilized to determine a medication recommendation, may be included with the recommendation as a justification for the recommendation.

Additionally, or alternatively, the recommendation(s) may include a potential gap in medical coverage. The one or more machine learning models may consider numerous factors associated with a patient to determine a potential gap in medical coverage, such as, for example, medications the patient takes, age of the patient, lab results associated with the patient, etc. These factors, that are utilized to determine a potential gap in medical coverage, may be included with the recommendation as a justification for the recommendation. For example, the remote computing resource(s) may determine that there is no data indicating that the patient has had a colonoscopy in the last 10 years. The remote system may then identify this as a potential gap in medical coverage for the patient, and include the potential gap in medical coverage as a recommendation to the medical professional to receive input regarding the potential gap in medical coverage.

The remote computing resource(s) may determine a prioritization associated with the recommendation(s) in a number of ways. In some examples, a prioritization of the recommendation(s) may be determined based on at least one of a medical severity associated with a recommendation (e.g., chronic conditions, acute conditions, etc.), information associated with the patient (e.g., age, gender, prior medical history, etc.), and information associated with the medical professional (e.g., historical usage data of the device, a schedule of the medical professional, etc.). Additionally, or alternatively, the prioritization of the recommendation(s) may be determined based on a first recommendation corresponding to a second recommendation. For example, if activities associated with completing tasks associated with the first recommendation complete activities associated with completing a task associated with a second recommendation, the remote computing resource(s) may lower a priority of the second recommendation, such that the tasks associated with the second recommendation have been completed. Additionally, or alternatively, the prioritization of the recommendation(s) may be determined based on an input received by a medical professional utilizing the device. For example, the medical professional may provide input associated with a first recommendation, and the remote computing resource(s) may determine that the input associated with the first recommendation is also associated with a second recommendation. The remote computing resource(s) may then determine a relevance of the input with respect to the second recommendation, and if the input is determined to satisfy a threshold relevance, lower a priority of the second recommendation. In some examples, the recommendation(s) may be prioritized dynamically, at run-time, such that while a medical professional is utilizing the device, the recommendation(s) may be re-ordered, replaced, and/or removed based on accepting/rejecting potential diagnosis and/or other input received from the device.

The remote computing resource(s) may utilize the prioritized tasks, medical professional profile data, and/or scheduling data associated with a medical service provider to throttle the recommendation(s), or task(s), such that a viable number of tasks is presented to a medical professional. For example, the remote computing resource(s) may throttle the prioritized recommendation(s) to determine a set of the medical recommendation(s) to send to the device and display to a medical professional. In some examples, the set may include any number of recommendation(s), such as, for example, 1, 2, 3, 4, 5, 10, 15, and so on. In some examples, the set of recommendation(s) may be determined based at least in part on an allotted amount of time for a scheduled patient visit, a number of appointments a medical professional has scheduled in a given day, and/or an amount of time between a patient's appointment and another patients appointment. Additionally, or alternatively, the set of recommendation(s) may be determined based at least in part on medical professional profile data, an amount of time that a medical service provider has utilized the device (for presenting the recommendation(s)), a total number of times that a medical professional has utilized the application, and/or a likelihood that the medical professional will utilize the recommendation(s).

The set of recommendation(s) may be redetermined dynamically, at run-time, such that while a medical professional is utilizing the device, the recommendation(s) may be re-ordered, replaced, and/or removed based on accepting/rejecting potential diagnosis and/or other input received from the device. For example, a medical professional may be presented with a set of medical recommendation(s), including a first medical recommendation associated with a potential diagnosis of diabetes, and a second medical recommendation associated with a potential diagnosis of obesity. The first potential diagnosis may include a justification as to why the remote computing resource(s) has determined the patient may have diabetes. Additionally, or alternatively, the first potential diagnosis may include a button to confirm the diagnosis, a button to reject the diagnosis, and/or a field for additional input. The remote system may receive the confirmation or rejection of the diagnosis and/or additional input entered by the medical professional on the device. In some examples, the remote system may determine a new set of medical recommendation(s) to present to the medical professional after receiving the confirmation or rejection of the first diagnosis and/or additional input. For example, the second medical recommendation associated with the potential diagnosis of obesity may no longer require action by the medical professional (e.g., communication between the medical professional and the patient) to determine if the potential diagnosis of obesity is confirmed or rejected, based on the previous input by the medical professional. In some examples, the second medical recommendation in the set of medical recommendation(s) may be replaced, or reprioritized, and a third medical recommendation may then be presented to the medical professional.

The device may display the recommendation(s) to a medical professional utilizing the device during a patient examination. The device may display the recommendation(s) in a number of ways. In some examples, the device may display the recommendation(s) in a categorized manner, such that each recommendation is prioritized based on its associated classification of one of a potential diagnosis, a medication recommendation, or a potential gap in medical coverage. Additionally, or alternatively, the classifications may be actionable such that each of the potential diagnosis, the medication recommendation, or the potential gap in medical coverage may be presented as a collapsible list. Additionally, or alternatively, the device may display task(s) associated with the recommendation(s). Additionally, or alternatively, a medical professional may select a recommendation to view additional information associated with the recommendation and/or the patient. In some examples, the recommendation(s) include corresponding justifications, presenting information indicating how the remote computing resource(s) determined to present the recommendation to the medical professional. In some examples, the most relevant portions of the justifications may be highlighted such that a medical professional is not required to read through all of the justifying information of the recommendation.

Compared to conventional techniques, which include predefined or static recommendation(s), and fail to provide a realistic number of recommendation(s) given the extent of a patient examination, the process described herein provides for the real-time generation and transmittal of recommendation(s) and throttling tasks associated with the recommendations. Such real-time information being properly prioritized is crucial given the time-sensitive interaction with patients and the time-sensitive nature of diagnosing patients. In other words, as medical professionals often have limited time with patients, the recommendation(s) must be generated substantially quickly and organized efficiently such that the medical professional can quickly identify the relevant information. By way of comparison, if the information is simply listed alphabetically or organized in an order that the tests were performed, the medical professional may not see the most relevant recommendation, resulting in inefficiency's that may potentially harm the patient. Instead the system and methods described herein allow for the time-sensitive generation, dynamic prioritization, and transmittal of recommendation(s). Moreover, through analyzing the user profiles, medical professional profiles, and the databases, the instant application allows for identification of potentially harmful diagnosis that may have been otherwise deprioritized and scheduled for later visit. The analysis performed by the machine learning model in generating trends, historical models, comparing user profiles, comparing medical professional profiles, comparing database(s) would not otherwise be possible in conventional methods given the vast amount of information that is required to be analyzed in such a time-sensitive manner.

The present disclosure provides an overall understanding of the principles of the structure, function, manufacture, and use of the systems and methods disclosed herein. One or more examples of the present disclosure are illustrated in the accompanying drawings. Those of ordinary skill in the art will understand that the systems and methods specifically described herein and illustrated in the accompanying drawings are non-limiting embodiments. The features illustrated and/or described in connection with one embodiment may be combined with the features of other embodiments, including as between systems and methods. Such modifications and variations are intended to be included within the scope of the appended claims. Additional details are described below with reference to several example embodiments.

Illustrative Environment

FIG. 1 shows an illustrative environment 100 which may include a provider 102 and a patient 104. In some instances, the environment 100 may be located at a medical facility (e.g., hospital, clinic, etc.) or at a residence of the patient 104. The environment 100 may also include a device 106 with which the provider 102, or in some instances, the patient 104 may interact. In the illustrative implementation, the provider 102 is holding the device 106. In other implementations, the patient 104 may hold the device 106. Further, more than one device 106 may be included within the environment 100. For instance, the provider 102 may have a device 106 while the patient 104 may have a separate device 106. In such instances, the devices may be configured to communicate with one another.

The device 106 may include a display 108 to display content. In some instance, the display 108 may include a touchscreen capable of receiving input from the provider 102 (or the patient 104). For instance, the display 108 may include a graphical user interface (GUI) that receives input from the provider 102. The display 108 may also include a virtual keyboard, buttons, input fields, and so forth, to permit the provider 102 to interact with the device 106.

The device 106 includes processor(s) 110 and memory 112. Discussed in detail herein, the processor(s) 110 may configure the device 106 to present a viable number of recommendation(s) in a prioritized manner on the display 108. Additionally, or alternatively, the device 106 may present justification(s) associated with the recommendation(s) on the display 108. Therein, the provider 102 may determine an accuracy of the recommendation(s) based on the justification(s) and address the patient 104, may perform examination(s) or diagnostics related to the recommendation(s), and/or enter an input on the device 106. For instance, FIG. 1 illustrates the provider 102 interacting with the patient 104. The device 106 may present a recommendation (e.g., potential diagnosis, gap in medical coverage, medication recommendation, etc.) as well as a justification associated with the recommendation (e.g., test results, medical history, personal information, identifying information associated with test results, a name of a company performing the tests, etc.). The provider 102 may select one of the justifications listed on the display 108 as being of particular relevance in determining that the recommendation is accurate. The input received by the device 106 may be transmitted to the remote computing resource 114.

The device 106 may be communicatively coupled to one or more remote computing resource(s) 114 to receive the recommendation(s). Additionally, the device 106 may transmit inputs from the provider 102 to the remote computing resource(s) 114. The remote computing resource(s) 114 may be remote from the environment 100 and the device 106. For instance, the device 106 may communicatively couple to the remote computing resource(s) 114 over a network 116. In some instances, the device 106 may communicatively couple to the network 116 via wired technologies (e.g., wires, USB, fiber optic cable, etc.), wireless technologies (e.g., RF, cellular, satellite, Bluetooth, etc.), or other connection technologies. The network 116 is representative of any type of communication network, including data and/or voice network, and may be implemented using wired infrastructure (e.g., cable, CAT5, fiber optic cable, etc.), a wireless infrastructure (e.g., RF, cellular, microwave, satellite, Bluetooth, etc.), and/or other connection technologies.

The remote computing resource(s) 114 may be implemented as one or more servers and may, in some instances, form a portion of a network-accessible computing platform implemented as a computing infrastructure of processors, storage, software, data access, and so forth that is maintained and accessible via a network such as the Internet. The remote computing resource(s) 114 do not require end-user knowledge of the physical location and configuration of the system that delivers the services. Common expressions associated with these remote computing resource(s) 114 may include "on-demand computing," "software as a service (SaaS)," "platform computing," "network-accessible platform," "cloud services," "data centers," and so forth.

The remote computing resource(s) 114 include a processor(s) 118 and memory 120, which may store or otherwise have access to one or more user profile(s) 122, one or more medical professional profile(s) 124, and/or one or more database(s) 126. Discussed in detail herein, the remote computing resource(s) 114 may generate, dynamically prioritize, and transmit the recommendation(s) to the device 106. Additionally, or alternatively, the remote computing resource(s) 114 may generate justification(s) associated with the recommendation(s), and transmit the justification(s) to the device 106. Additionally, the remote computing resource(s) 114 may utilize the user profile(s) 122, the medical professional profiles, and/or the database(s) 126.

As used herein, a processor, such as processor(s) 110 and/or 118, may include multiple processors and/or a processor having multiple cores. Further, the processors may comprise one or more cores of different types. For example, the processors may include application processor units, graphic processing units, and so forth. In one implementation, the processor may comprise a microcontroller and/or a microprocessor. The processor(s) 110 and/or 118 may include a graphics processing unit (GPU), a microprocessor, a digital signal processor or other processing units or components known in the art. Alternatively, or in addition, the functionally described herein can be performed, at least in part, by one or more hardware logic components. For example, and without limitation, illustrative types of hardware logic components that may be used include field-programmable gate arrays (FPGAs), application-specific integrated circuits (ASICs), application-specific standard products (ASSPs), system-on-a-chip systems (SOCs), complex programmable logic devices (CPLDs), etc. Additionally, each of the processor(s) 110 and/or 118 may possess its own local memory, which also may store program components, program data, and/or one or more operating systems.

The memory 112 and/or 120 may include volatile and nonvolatile memory, removable and non-removable media implemented in any method or technology for storage of information, such as computer-readable instructions, data structures, program component, or other data. Such memory 112 and/or 120 may include, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, RAID storage systems, or any other medium which can be used to store the desired information and which can be accessed by a computing device. The memory 112 and/or 120 may be implemented as computer-readable storage media ("CRSM"), which may be any available physical media accessible by the processor(s) 110 and/or 118 to execute instructions stored on the memory 112 and/or 120. In one basic implementation, CRSM may include random access memory ("RAM") and Flash memory. In other implementations, CRSM may include, but is not limited to, read-only memory ("ROM"), electrically erasable programmable read-only memory ("EEPROM"), or any other tangible medium which can be used to store the desired information and which can be accessed by the processor(s).

Illustrative Remote Computing Resources

Figure 2:
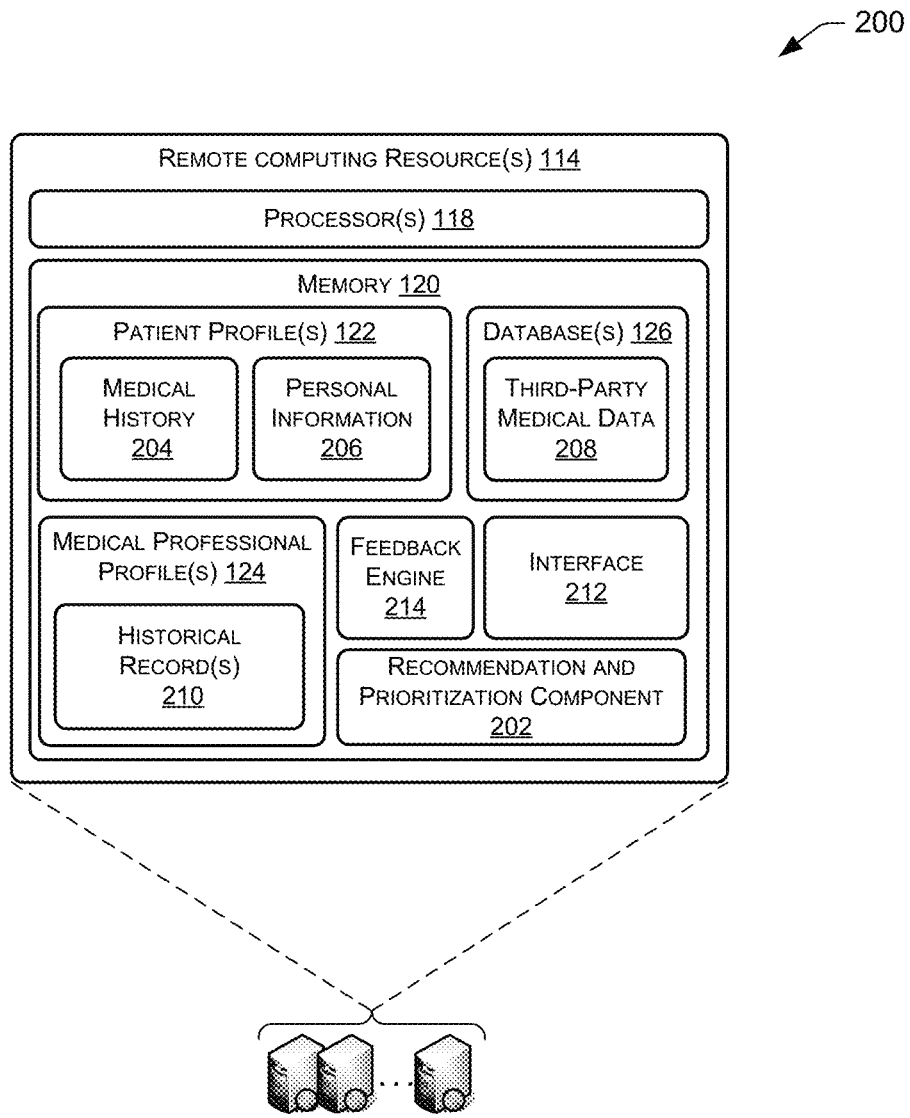
FIG. 2 illustrates a block diagram of functional components of an example remote computing resource of FIG. 1.

FIG. 2 illustrates an example block diagram 200 of functional components of an example remote computing resource(s) 114. The remote computing resource(s) 114 includes the processor(s) 118 and the memory 120. As illustrated, the memory 120 of the remote computing resource(s) 114 stores or otherwise has access to patient profile(s) 122, the medical professional profiles 124, the database(s) 126, and a recommendation and prioritization component 202. The patient profile(s) 122 may correspond to a respective patient. Each patient profile 122 may include a patient's medical history 204 and personal information 206. In some instances, the medical history 204 may include a medical history of the patient, such as diagnoses (e.g., disease, illness, etc.), treatments (e.g., medications, surgeries, therapy, etc.), family medical history (e.g., diabetes, Alzheimer's, etc.), measurements (e.g., weight, height, etc.), symptoms (e.g., sore throat, back pain, loss of sleep, etc.), and so forth. The personal information 206 may include names (e.g., social security number (SSN)), identifiers, residence, work history, acquaintances, heritage, age, and so forth. The medical history 204 and/or the personal information 206 may be received using record locators and/or searching databases.

The database(s) 126 may include information or third-party medical data 208 obtained from third-party sources. The third-party sources may include a source (or service) that collects, stores, generates, filters, and/or provides medical news. In some instances, the third-party sources that provide the third-party medical data 208 may include governmental agencies or services (e.g., U.S. Department of Health and Human Services (HHS), Centers for Disease Control and Prevention (CDC), National Institute of Health (NIH), etc.), medical new websites or sources (e.g., webmd.com, etc.), other medical sources (e.g., American Red Cross, Universities, Hospitals, etc.). The third-party medical data 208 may also include data obtained from other online resources that search for content, such as medical information. For instance, the online resources may include, but are not limited to, search engines (e.g., GOOGLE®), social media sites (e.g., FACEBOOK®, INSTRAGRAM®, etc.), databases, and/or other online resources. The remote computing resource(s) 114 may be in communication with the third-party sources to obtain, retrieve, and/or receive the third-party medical data 208 representing medical situations, medical conditions, and/or medical news.

As noted above, the remote computing resource(s) 114 may analyze the user profile(s) 122 and/or the database(s) 126 to generate recommendation(s) for a patient. For instance, the recommendation and prioritization component 202 may analyze the user profile(s) 122, the medical professional profile(s) 124, and/or the database(s) 126 to determine recommendation(s) to present to a healthcare professional. The recommendation and prioritization component 202 may also be configured to prioritize the recommendation(s) ensuring a particular medical professional, such as provider 102, is aware of the most severe medical conditions of the patient. Additionally, or alternatively, the recommendation and prioritization component may present only viable number of the recommendation(s), or a set, that a medical professional can complete in the time allotted for a patient examination. Additionally, or alternatively, the recommendation and prioritization component 202 functions to determine recommendations, such as suspected diagnoses of the patient (e.g., diabetes, heart disease, etc.), potential gaps in coverage (e.g., mammograms) associated with the patient, and/or a medication recommendation for the patient, that should be asked of the patient in determining one or more suspected health concerns (or diagnoses) of the patient or whether the patient is suspected of having particular diagnoses. For instance, based on analyzing the patient profile(s) 122, the medical professional profile(s) 124, and/or the database(s) 126, the prediction analytics component 202 may identify suspected diagnoses of the patient. In some instances, the analysis may involve comparing symptoms stored in the patient profile(s) 122 to the database(s) 126 (or other patient profile(s) 122) to determine correlations between the patient's symptoms and one or more suspected diagnoses. That is, continuing with the above example, based on the analysis, the recommendation and prioritization component 202 may determine that symptoms of a patient correlate closely with one or more diagnoses.

Additionally, or alternatively, the recommendation and prioritization component 202 may determine the suspected diagnoses despite the user profile(s) 122 failing to indicate such diagnoses. For instance, the user profile 122 of a patient may indicate two distinct symptoms, such as a first symptom (e.g., high blood sugar levels) and a second symptom (e.g., skin infections). These symptoms may be analyzed by the prediction analytics component 202 to determine that the patient is suspected of having diabetes. However, taken individually, these symptoms may fail to indicate that diabetes is a suspected diagnosis. In other words, individually, the first symptom and the second symptom may not indicate that the patient has diabetes and/or the first symptom and the second symptom may not indicate the probability of the suspected diagnosis over a threshold. Using the recommendation and prioritization component 202, the symptoms of a patient may be aggregated and correlated to symptoms associated with a suspected diagnosis (e.g., diabetes). That is, when looked at collectively, the recommendation and prioritization component 202 may determine that the first symptom and the second symptom may be indicative of diabetes. Using this determination, the recommendation and prioritization component 202 may determine a statistical relevance of the information used to make the recommendation(s).

The recommendation(s) generated are a result of the outcomes of the recommendation and prioritization component 202 utilizing one or more predictive analytic techniques, which may include, for example, predictive questioning, machine learning, and/or data mining. Generally, predictive questioning may utilize statistics to predict outcomes and/or question(s) to propose in future. Machine learning, while also utilizing statistical techniques, provides the ability to improve outcome prediction performance without being explicitly programmed to do so. Any number of machine learning techniques may be employed to generate and/or modify the recommendation(s) describes herein. Those techniques may include, for example, decision tree learning, association rule learning, artificial neural networks (including, in examples, deep learning), inductive logic programming, support vector machines, clustering, Bayesian networks, reinforcement learning, representation learning, similarity and metric learning, sparse dictionary learning, and/or rules-based machine learning.

Once the recommendation(s) have been generated, the recommendation and prioritization component 202 may determine a prioritization of the recommendation(s). The recommendation and prioritization component 202 may determine the prioritization of the recommendation(s) based on a medical severity associated with the recommendation(s). Additionally, or alternatively, the recommendation and prioritization component 202 may determine a prioritization for the recommendation(s) based on an importance to the patient associated with the recommendation(s). Additionally, or alternatively, the recommendation and prioritization component 202 may determine a prioritization of the recommendation(s) based on a medical provider's prior interaction with the patient and previous recommendation(s) (e.g., historical use of the recommendation(s) to suggest treatment plans for a patient, based on the recommendation(s)). The recommendation and prioritization component 202 may determine the prioritization utilizing a combination of any of the techniques listed above; however, is not limited to determining the prioritization of the recommendation(s) based on the techniques above, and may determine the prioritization of the recommendation(s) based on other factors such as, for example, recommendation(s) associated with other patients, trends in recommendation(s), and/or any other statistical indication obtained utilizing the data the remote computing resource(s) 114 has access to.

In some examples, the recommendation and prioritization component 202 may determine the prioritization of the recommendation(s) based on a medical severity associated with the recommendation(s). For example, the recommendation and prioritization component 202 may determine that a recommendation associated with a colon cancer screening (e.g., the remote computing resource(s) have no records of the patient having a screening in a suggested time period) is more severe than a recommendation associated with changing a patients prescription from a 30-day refill to a 90-day refill. Accordingly, the recommendation and prioritization component 202 may prioritize the recommendation associated with the colon cancer screening above (or favor) the recommendation associated with the prescription change.

In some examples, the recommendation and prioritization component 202 may determine the prioritization of the recommendation(s) based on an importance of a recommendation to a patient. In some examples, the recommendation and prioritization component 202 may determine an importance of a recommendation to the patient by accessing the patient profile(s) 122 to analyze the medical history 204 and personal information 206 associated with a patient. Additionally, or alternatively, the recommendation and prioritization component 202 may determine an importance of the recommendation to the patient by analyzing third-party medical data 208 stored in the database(s) 126 of the remote computing resource(s) 114. For example, the recommendation and prioritization component 202 may determine a recommendation associated with a potential diagnosis of congestive heart failure is more important to a patient than a recommendation associated with a potential diagnosis of diabetes, based on the patient's medical history 204 indicating that congestive heart failure has a history in their family. Accordingly, the recommendation and prioritization component 202 may prioritize the recommendation associated with the potential diagnosis of congestive heart failure above (or favor) the recommendation associated with the potential diagnosis of diabetes.

In some examples, the recommendation and prioritization component 202 may determine a prioritization of the recommendation(s) based on a medical service provider's prior interaction with the patient and previous recommendation(s) (e.g., historical use of the recommendation(s) to suggest treatment plans for a patient, based on the recommendation(s)). In some examples, the recommendation and prioritization component 202 may determine a medical service provider's prior interaction with previous recommendation(s) by analyzing historical record(s) 210 stored in medical professional profile(s) 124. Additionally, or alternatively, the recommendation and prioritization component 202 may determine the medical service provider's prior interaction with previous recommendation(s) associated with the patient by analyzing the medical history 204 of a patient, and historical record(s) 210. For example, the recommendation and prioritization component 202 may determine that a medical professional associated with a medical service provider is likely to prescribe a medication recommendation generated by the recommendation and prioritization component 202 based on an analysis of the historical record(s) 204 stored in the medical professional profile 124 of the medical professional.

Once the recommendation and prioritization component 202 has determined a prioritization of the recommendation(s), the recommendation and prioritization component 202 may determine a number of recommendation(s) (or a set of medical recommendation(s)) to display to a medical professional during a patient examination. Given the length of a patient examination, and a number of examinations a patient has per year, this determination is very crucial to ensure the patient is receiving the proper care they need, and the medical professional is addressing the most important medical concerns. The number of recommendation(s) displayed to the medical professional, or included in the set, may be any number, for example, the number of recommendations may be any number from 1-X where X is any integer greater than 1. The recommendation and prioritization component 202 may determine the number of recommendation(s) based on an amount of time associated with the patient examination. Additionally, or alternatively, the recommendation and prioritization component 202 may determine the number of recommendation(s) based on a schedule associated with a medical professional and/or the medical service provider. Additionally, or alternatively, the recommendation and prioritization component 202 may determine the number of recommendation(s) based on a medical severity associated with the recommendation(s). Additionally, or alternatively, the recommendation and prioritization component 202 may determine the number of recommendation(s) based on a medical service provider's prior interaction with previous recommendation(s). The recommendation and prioritization component 202 may determine the number of recommendation(s) utilizing a combination of any of the techniques listed above; however, is not limited to determining the number of recommendation(s) of the recommendation(s) based on the techniques above, and may determine the prioritization of the recommendation(s) based on other factors such as, for example, historical data associated with examinations of other patients, trends in recommendation(s), and/or any other statistical indication obtained utilizing the data the remote computing resource(s) 114 has access to.

In some examples, the recommendation and prioritization component 202 may determine the number of recommendation(s) based on an amount of time associated with the patient examination. For example, for a patient examination scheduled for 15 minutes, the recommendation and prioritization component 202 may determine to display 5 recommendation(s) to a medical professional during the patient examination based on the duration of the appointment, and historical record(s) 210 in the medical professional profile of the associated professional indicating that, historically, that medical professional is able to complete 5 recommendation(s) in a 15 minute time period. Additionally, or alternatively, the recommendation and prioritization component 202 may utilize one or more patient profile(s) 122 to determine an average time to complete a specific recommendation, and the recommendation and prioritization component 202 may use the average time to complete the specific recommendation to determine the number of recommendation(s) to display to the medical professional during the patient examination.

In some examples, the recommendation and prioritization component 202 may determine the number of recommendation(s) based on a schedule associated with a medical professional and/or the medical service provider. For example, the recommendation and prioritization component 202 may determine the length of the patient examination and analyze the schedule of a medical professional for the remainder of the day. In some examples, a patient may have numerous highly prioritized medical recommendation(s) (e.g., recommendation(s) of importance to the patient), while the recommendation and prioritization component 202 may determine to display 5 recommendation(s) based on the length of the patient examination. Additionally, the recommendation and prioritization component 202 may determine that there is additional time after the patient examination, based on the analysis of the medical professional's schedule for the remainder of the day. In some examples, the recommendation and prioritization component 202 may determine to display additional recommendation(s) during the patient examination, based on identifying the additional time after the patient examination.

In some examples, the recommendation and prioritization component 202 may determine the number of recommendation(s) based on a medical severity associated with the recommendation(s). For example, the recommendation and prioritization component 202 may determine to display 5 recommendation(s) to the medical professional during the patient examination. The recommendation and prioritization component 202 may determine that a recommendation that is not included in the original set of 5 recommendation(s), and based on the medical severity, may replace a recommendation in the original set of 5 recommendation(s) having the lowest priority and/or medical severity with the recommendation that was not included in the original set of 5 recommendation(s).

In some examples, the recommendation and prioritization component 202 may determine the number of recommendation(s) based on a medical service provider's prior interaction with previous recommendation(s). For example, the recommendation and prioritization component 202 may determine to display 5 recommendation(s) to a medical professional during a patient examination based on an analysis of the historical record(s) associated with the medical professional profile 124 of the medical professional. In some examples, the recommendation and prioritization component 202 may determine the medical professional is likely to follow the recommendation(s) and suggest a treatment plan for a patient based on the recommendation(s), accordingly, the recommendation and prioritization component 202 may provide the top 5 medical recommendation(s) based on the priority. Additionally, or alternatively, the recommendation and prioritization component 202 may determine that the medical professional is unlikely to follow the recommendation(s) and may provide 5 recommendations that are more likely to be followed by the medical professional.

In some examples, the recommendation(s) and/or a prioritized set of the recommendation(s) may be transmitted to the device 106 in response to a pull request from the device 106. Additionally, or alternatively, the recommendation(s) and/or the prioritized set of the recommendation(s) may be pushed to the device 106 after generating the recommendation(s) and/or the prioritized set of the recommendation(s). The remote computing resource(s) 114 may transmit the recommendation(s) and/or the prioritized set of the recommendation(s) with a command that causes the device 106 to display the recommendation(s) and/or the prioritized set of the recommendation(s). To communicate with the device 106, the third-party sources providing the third-party data 206, or other entities, the remote computing resource(s) 114 include an interface 212.

The remote computing resource(s) 114 are configured to receive, from the device 106, prompts, messages, feedback, or response(s) (e.g., words, phrase, sentences, selections etc.) to the indicate which supporting evidence was used to determine if the recommendation is accurate. In some instances, the feedback may be received by a feedback engine 214 and/or the processor(s) 118 may forward the feedback to the historical records 210. Upon receiving the feedback, the feedback engine 214 may be configured to analyze the feedback to determine words, phrases, and expressions contained therein. For instance, the feedback may include an indication of which of the recommendation(s) were accurate. The recommendation and prioritization component 202 may utilize the feedback to prioritize recommendations and determine a number of recommendations to include in a set to transmit and present to a medical professional during a patient examination.

The recommendation and prioritization component 202 may also reference other diagnoses and/or systems stored in other patient profile(s) 122. In this sense, the recommendation and prioritization component 202 may compare symptoms of a respective patient with symptoms experienced by other patients in determining suspected diagnoses and mapping the patient profile(s) 122 together and analyzing trends. For instance, other patients may have experienced similar symptoms as the patient and the recommendation and prioritization component 202 may use these indications to determine suspected diagnoses of the patient. In some instances, the amount of influence this factor has may decay over time. For instance, if two patients are experiencing similar symptoms and one was diagnosed with diabetes within a year, then the recommendation and prioritization component 202 may weight this interaction more greatly than if the diagnosis was several years prior.

The patient profile(s) 122, the medical professional profile(s) 124, and/or the database(s) 126 may be updated based on the recommendation(s), such as, for example, symptoms indicated by the recommendation(s). Additionally, in some examples, the remote computing resource(s) 114 may obtain, retrieve, and/or receive the medical history 204, the personal information 206, the historical records 210, and/or the third-party medical data 208 continuously from the third-party sources. In some examples, the remote computing resource(s) 114 may obtain, retrieve, and/or receive the medical history 204, the personal information 206, the historical records 210, and/or the third-party medical data 208 at given time intervals. The given time intervals may include, but are not limited to, every minute, half-hour, hour, day, week, month, or the like.

Additionally, to protect the privacy of information contained in the patient profile(s) 122, the remote computing resource(s) 114 may receive consent from patients to share, correlate, or otherwise use the information in determine one or more suspected diagnoses. That is, as noted above, the remote computing resource(s) 114 may correlate symptoms of one patient with symptoms or another patient in determining recommendation(s) and a prioritization of the recommendation(s). Before such correlation of comparisons, the remote computing resource(s) 114 may first receive consent.

Illustrative Device

Figure 3:
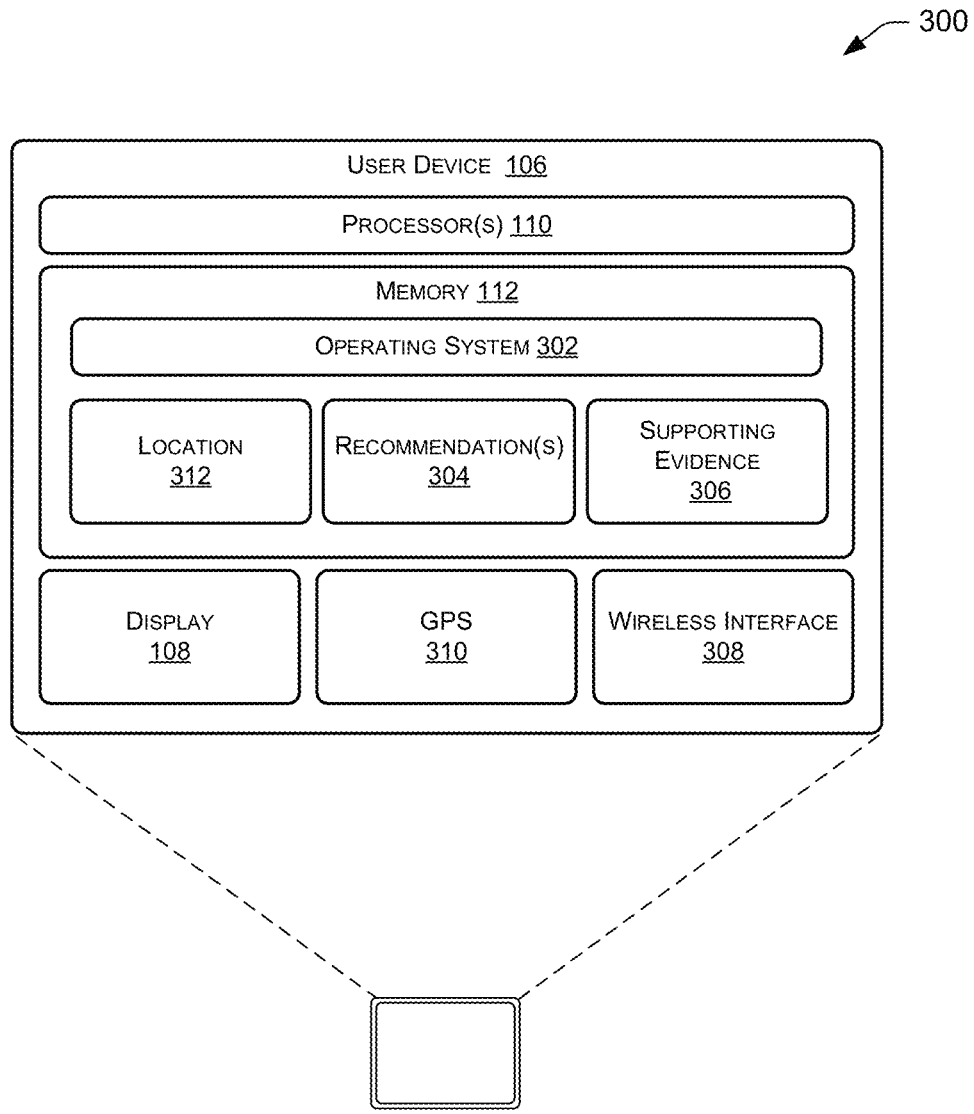
FIG. 3 illustrates a block diagram of functional components of an example device of FIG. 1.

FIG. 3 illustrates an example block diagram 300 of functional components of an example device 106. Generally, the device 106 may be implemented as a standalone device that is relatively simple in terms of functional capabilities with input/output components, memory (e.g., the memory 112), and processing capabilities. For instance, the device 106 may include the display 108 or a touchscreen to facilitate visual presentation (e.g., text, charts, graphs, images, etc.), graphical outputs, and receive user input through touch inputs on the display 108 (e.g., virtual keyboard).

The memory 112 stores an operating system 302. The operating system 302 may configure the processor(s) 110 to display recommendation(s) 304 and supporting evidence 306 associated with the recommendation(s) 304 on the display 108. Display of the recommendation(s) 304 and supporting evidence 306 associated with the recommendation(s) 304 may involve displaying selectable text where a user (e.g., provider 102) is able to provide input, as shown and discussed below in FIG. 6. In some instances, multiple recommendation(s) 304 and supporting evidence 306 associated with the recommendation(s) 304 may be displayed in unison, or at the same time on the display 108, or only one recommendation 304 and supporting evidence 306 associated with the recommendation 304 may be presented at a time on the display 108. Further, the device 106 may be configured to transmit one or more user input at the same time, or user input may be submitted individually.

In the illustrated example, the device 106 includes a wireless interface 308 to facilitate a wireless connection to a network (e.g., the network 116) and the remote computing resource(s) 114. The wireless interface 308 may implement one or more of various wireless technologies, such as WiFi, Bluetooth, RF, and the like.

FIG. 3 also illustrates that the device 106 may include global positioning systems (GPS) 310 or other locating devices may be used. The GPS 310 may generate a location 312 that corresponds to a location of the device 106. In some instances, the processor(s) 110 may utilize the location 312 in downloading or receiving the recommendation(s) 304 and supporting evidence 306 associated with the recommendation(s) 304 from the remote computing resource(s) 114. For instance, the location 312 may indicate that the device 106 is within a residence of a patient or a threshold proximity thereof. In response, the processor(s) 110 may receive (e.g., download) the recommendation(s) 304 and supporting evidence 306 associated with the recommendation(s) 304 from the remote computing resource(s) 114. In another instance, the location 312 may indicate the device 106 is traveling towards the residence of the patient, and in response, the device 106 may receive the recommendation(s) 304 and supporting evidence 306 associated with the recommendation(s) 304. As noted above, however, to receive the recommendation(s) 304 and supporting evidence 306 associated with the recommendation(s) 304, the processor(s) 110 may transmit a pull request, or the remote computing resource(s) 114 may push the recommendation(s) 304 and supporting evidence 306 associated with the recommendation(s) 304 in response to determining the device 106 is within the residence or is in route to the patient's residence.

In some instances, the device 106 may include one or more microphones that receive audio input, such as voice input from the provider 102 and/or the patient 104, and one or more speakers to output audio. For instance, the provider 102 or the patient 104 may interact with the device 106 by speaking to it, and the one or more microphone captures the user speech. In response, the device 106 performs speech recognition (e.g., speech recognition engine and/or speech-to-text) and types text data into a field corresponding to the speech. Additionally, or alternatively, the audio data may be provided to the remote computing resource(s) 114 as user input, where the remote computing resource(s) 114 analyzes the user input. To relay the recommendation(s) 304 and supporting evidence 306 associated with the recommendation(s) 304 to the patient 104, the device 106 may emit audible statements through the speaker. In this manner, and in some instances, the provider 102 and/or the patient 104 may interact with the device 106 through speech, without using and/or in addition to the virtual keyboard presented on the display 108, for instance.

In some instances, the memory 112 may include the patient profile(s) 122, the medical professional profile(s) 124, the databases 126, the recommendation and prioritization component 202, and/or the feedback engine 214. Additionally, at least some of the processes of the remote computing resource(s) 114 may be executed by the device 106.

Illustrative Processes

Figure 4:
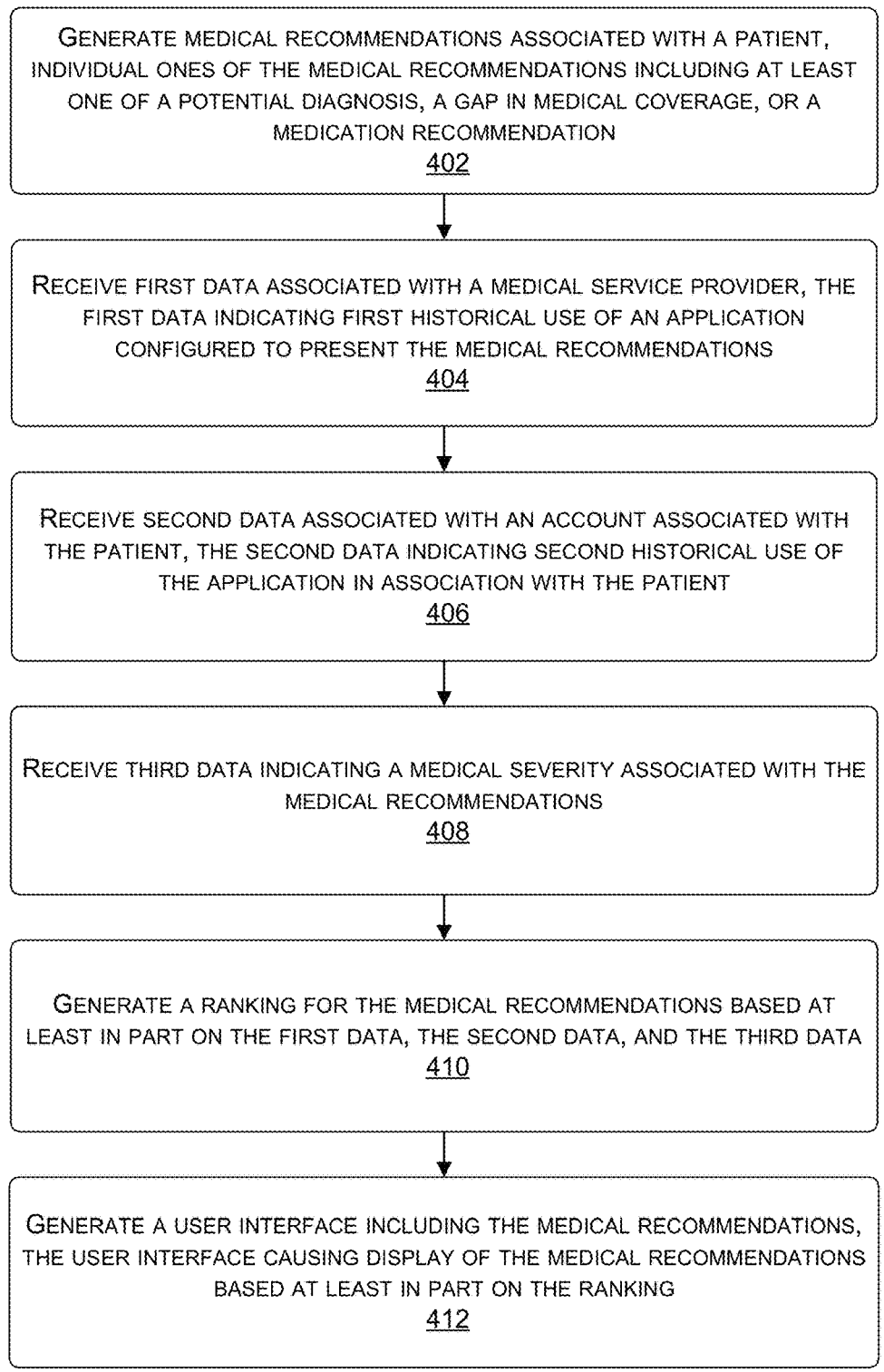
FIG. 4 illustrates a flow diagram of an example method for the remote computing resource(s) of FIG. 1 to prioritize medical recommendations.

FIGS. 4 and 5 illustrate various processes related to prioritizing medical recommendations and prioritizing and determining a set of medical recommendation(s) to display to a medical professional during a patient examination. The processes described herein are illustrated as collections of blocks in logical flow diagrams, which represent a sequence of operations, some or all of which may be implemented in hardware, software, or a combination thereof. In the context of software, the blocks may represent computer-executable instructions stored on one or more computer-readable media that, when executed by one or more processors, program the processors to perform the recited operations. Generally, computer-executable instructions include routines, programs, objects, components, data structures and the like that perform particular functions or implement particular data types. The order in which the blocks are described should not be construed as a limitation, unless specifically noted. Any number of the described blocks may be combined in any order and/or in parallel to implement the process, or alternative processes, and not all of the blocks need be executed. For discussion purposes, the processes are described with reference to the environments, architectures and systems described in the examples herein, such as, for example those described with respect to FIGS. 1-3 and 6, although the processes may be implemented in a wide variety of other environments, architectures and systems.

FIG. 4 illustrates a flow diagram of an example method 400 for one or more remote computing resource(s) 114 to determine medical recommendation(s) and prioritize the medical recommendation(s) to send to a device 106 for presentation to a medical professional.

At block 402, one or more remote computing resource(s) 114 may generate medical recommendation(s) associated with a patient, individual ones of the medical recommendation(s) may include at least one of a potential diagnosis, a gap in medical coverage, and/or a medication recommendation. In some examples, the remote computing resource(s) 114 generate the medical recommendation(s) using any of the methods described above with respect to FIGS. 1-3.

At block 404, the remote computing resource(s) 114 may receive first data associated with a medical service provider. The first data may indicate first historical use of an application configured to present the medical recommendation(s). In some examples, the first data may include the historical record(s) 210 associated with the medical professional profile(s) 124.

At block 406, the remote computing resource(s) 114 may receive second data associated with an account associated with the patient. The second data may indicate second historical use of the application in association with the patient. In some examples, the second data may include the medical history 204 and/or the personal information 206 associated with patient profile(s) 122.

At block 408, the remote computing resource(s) 114 may receive third data indicating a medical severity associated with the medical recommendation(s). In some examples, the third data may include the third-party medical data 208 stored in the one or more database(s) 126 of the remote computing resource(s) 114.

At block 410, the remote computing resource(s) 114 may generate a ranking for the medical recommendation(s). In some examples, the remote computing resource(s) 114 may generate the ranking based on the first data, the second data, and/or the third data. In some examples, the remote computing resource(s) may dynamically generate the ranking at run-time, and while a medical professional is utilizing the recommendation(s). The remote computing resource(s) 114 may generate the ranking using any of the methods described above with respect to FIGS. 1-3.

At block 412, the remote computing resource(s) 114 may generate a user interface to present on the display 108 of the device 106. In some examples, the user interface may include the medical recommendation(s). Additionally, or alternatively, the user interface may cause the medical recommendations to be displayed based on the ranking of the medical recommendation(s).

FIG. 5 illustrates a process 500 for determining medical recommendation(s), prioritizing the medical recommendation(s), and determining a set of the medical recommendation(s) to present to a medical professional during a patient examination.

At block 502, the remote computing resource(s) 114 may generate medical recommendation(s) associated with a patient, individual ones of the medical recommendation(s) may include at least one of a potential diagnosis, a gap in medical coverage, and/or a medication recommendation. The medical recommendations may be associated with a ranking based at least in part on first data indicating first historical use, by a medical service provider, of an application configured to present the medical recommendation(s). Additionally, or alternatively, the ranking may be based at least in part on second data indicating second historical use of the application in association with the patient. In some examples, the remote computing resource(s) may dynamically generate the ranking at run-time, and while a medical professional is utilizing the recommendation(s). In some examples, the remote computing resource(s) 114 generate the one or more medical recommendation(s) using any of the methods described above with respect to FIGS. 1-3.

At block 504, the remote computing resource(s) 114 may receive third data indicating a schedule associated with the medical provider. In some examples, the schedule may include appointments including a first appointment associated with the patient. In some examples, the first appointment may indicate a duration of time scheduled for the first appointment. In some examples, the third data includes the medical professional profile(s) 124 associated with the medical provider. Additionally, or alternatively, the third data may include a number of appointments scheduled during a day, a number of appointments associated with a patient scheduled during a year, and/or an amount of time between the first appointment and a second appointment scheduled after the first appointment.

At block 506, the remote computing resource(s) 114 may determine a set of medical recommendations from the medical recommendations to present to on a user interface of the device 106 during the first appointment. In some examples, the set may be determined based on the first data, the third data, and/or the ranking. Additionally, or alternatively, the remote computing resources may determine a number of recommendation(s) from the medical recommendations to present to the medical professional during the patient examination. The remote computing resource(s) 114 may determine the set of medical recommendation(s) and/or determine the number of recommendation(s) to present using any of the methods described above with respect to FIGS. 1-3.

At block 508, the remote computing resource(s) 114 may generate a user interface to present on the display 108 of the device 106. In some examples, the user interface may include the set of the medical recommendation(s). Additionally, or alternatively, the user interface may cause the set of medical recommendations to be displayed during the first appointment.

Figure 6:
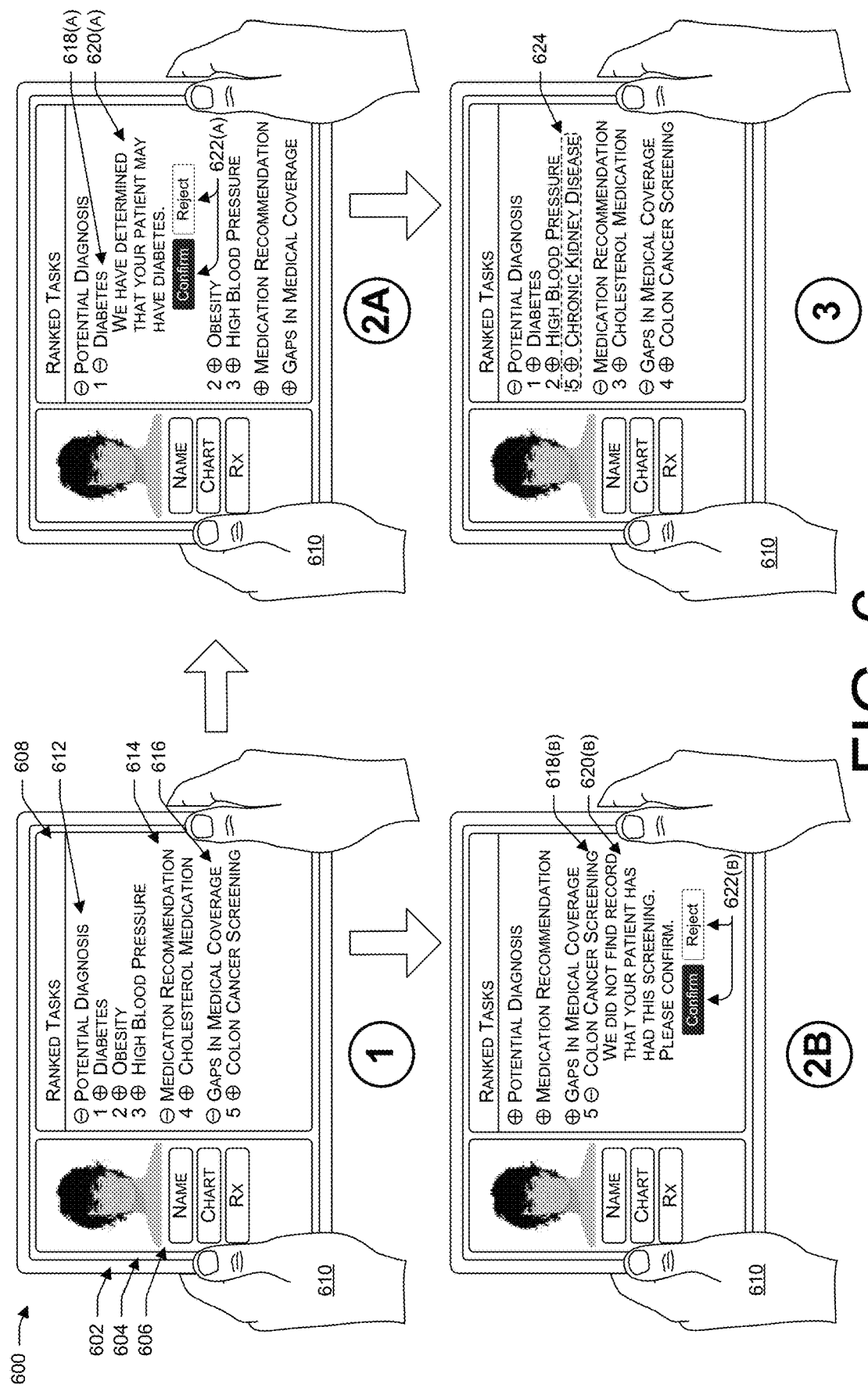
FIG. 6 illustrates an example flow of a medical professional interacting with the device of FIG. 1 to display medical recommendations and throttle tasks to prioritize the medical recommendations.

FIG. 6 illustrates an example flow 600 of a medical professional interacting with a device 602 (which may be similar to and/or represent the device 106) displaying recommendations(s) in a prioritized manner. The progression of the flow shown in FIG. 6 is illustrated by the arrows.

The device 602 is shown including a display 604 having a first area 606 and a second area 608. In the first area 606, background information of a patient is displayed. For instance, the first area 606 may include an image of the patient, a name of the patient, medical charts of the patient, or prescriptions of the patient. However, while FIG. 6 illustrates certain background information, other information may be displayed as well, or the background information may be presented differently than shown. The background information may be accessed through a user 610 interacting with the display 604. For instance, the user 610 may select "Chart" within the first area and medical charts of the patient may be displayed on the display 604.

Shown at "1," the second area 608 displays a number of recommendation categories that may be selectable by the user 610. In this example, the recommendation categories include one or more potential diagnoses 612, medication recommendation(s) 614, and/or potential gap(s)-in-coverage 616 in a prioritized manner. In some examples, the recommendation categories may be sorted in any order. Additionally, or alternatively, the recommendation(s) may be presented in a prioritized manner without the recommendation categories. The user 610 may expand any one of the recommendation categories to view one or more recommendations of that category. For example, the potential diagnosis recommendation category 612 may include one or more potential diagnosis of the patient, such as, for example, diabetes, obesity, and/or high blood pressure, and the like. Additionally, or alternatively, the one or more recommendation(s) included in a recommendation category 612, 614, 616, may be selectable by the user 610. For example, each recommendation may be selectable which causes the device 602 to present additional information associated with the recommendation. Additionally, or alternatively, each recommendation may include an indicator in proximity of the recommendation indicating if the selectable recommendation has been expanded to show additional information (−) or if the selectable recommendation has not been expanded to show the additional information (+).

As shown at "2A," the device 602 displays a potential diagnosis of diabetes 618(A) that has been selected by the user 610. The selected potential diagnosis of diabetes 618(A) may include additional information 620(A) associated with the potential diagnosis of diabetes 618(A) recommendation. In some examples, the additional information 620(A) may include supporting evidence and/or justifications associated with the medical recommendation, as described above with respect to FIGS. 1-3. Additionally, or alternatively, the selected potential diagnosis of diabetes 618(A) may include one or more buttons 622(A) for confirming or rejecting the potential diagnosis of diabetes 618(A). Additionally, or alternatively, the selected potential diagnosis of diabetes 618(A) may include an area for a medical professional to provide text feedback and/or additional information associated with the potential diagnosis of diabetes 618(A).

Additionally, or alternatively, as shown at "2B", the device 602 displays a potential gap in medical coverage of a colon cancer screening 618(B) that has been selected by the user. The selected potential gap in medical coverage of a colon cancer screening 618(B) may include additional information 620(B). In some examples, the additional information 620(B) may include supporting evidence and/or justifications associated with the medical recommendation, as described above with respect to FIGS. 1-3. Additionally, or alternatively, the potential gap in medical coverage of a colon cancer screening 618(B) may include one or more buttons 622(B) for confirming or rejecting the potential gap in medical coverage of a colon cancer screening 618(B). Additionally, or alternatively, the potential gap in medical coverage of a colon cancer screening 618(B) may include an area for a medical professional to provide text feedback and/or additional information associated with the potential gap in medical coverage of a colon cancer screening 618(B).

As shown at "3," the device 602 displays the medical recommendation(s) including a new medical recommendation 624 associated with chronic kidney disease replacing a medical recommendation associated with obesity that was previously displayed. The new medical recommendation 624 may be a result of the medical professional confirming or rejecting the potential diagnosis of diabetes 618(A) as shown at "2A," by selecting the one or more buttons 622(A). In some examples, the remote computing resource(s) 114 may receive the input from the device 106 and determine that, based on the input, the remote computing resource(s) 114 can confirm or reject the medical recommendation associated with obesity that was previously displayed without any action by the medical professional. In some examples, the remote computing resource(s) 114 may determine a new medical recommendation 624 now has a higher priority than the medical recommendation associated with obesity, and replace the medical recommendation associated with obesity with the new medical recommendation 624. The remote computing resource(s) 114 may replace any of the recommendations with a new medical recommendation using any of the methods described above with respect to FIG. 2.

Figure 7:
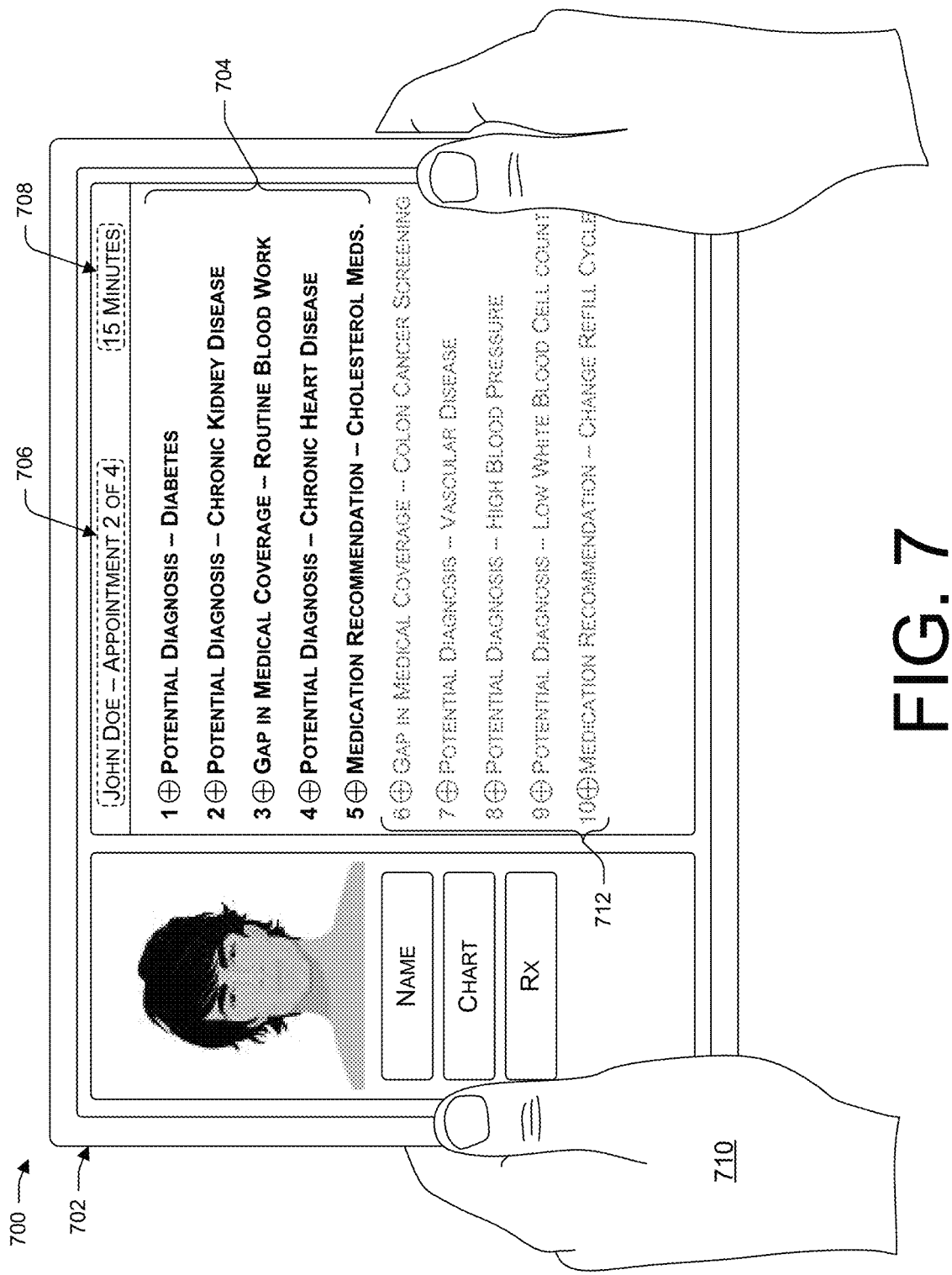
FIG. 7 illustrates an example diagram of a medical professional interacting with a user interface of an example device of FIG. 1 displaying a throttled set of recommendations during a patient examination.

FIG. 7 illustrates an example diagram 700 of a medical professional interacting with a user interface of a device 702 (which may be similar to and/or represent the device 106) displaying a set of throttled recommendation(s) 704 during a patient examination.

The device 702 may include similar elements as device 602, such as, for example, a display 604 having a first area 606 and a second area 608. Additionally, or alternatively, the device 702 may include similar functionality as device 602, such as, for example the recommendations may be selectable by a user 710 to present additional information associated with each recommendation. Additionally, or alternatively, each recommendation may include an indicator in proximity of the recommendation indicating if the selectable recommendation has been expanded to show additional information (−) or if the selectable recommendation has not been expanded to show the additional information (+). In some examples, when a user 710 selects a recommendation, background information, supporting evidence, justifications, and/or actionable buttons may be presented in association with the selected recommendation. Additionally, the device 702 may display the medical recommendation(s) in a throttled manner, where the recommendation(s) are prioritized, or a set of the recommendation(s) is presented to the user without being organized by recommendation category (e.g., potential diagnosis, gaps in medical coverage, and/or medication recommendation). Additionally, or alternatively, the device 702 may display schedule information associated with the patient, such as, for example, an appointment indication 706, and/or a duration of the appointment 708.

In some examples, the appointment indication 706 may display information including, but not limited to, an indication of the patient, an appointment number associated with the patient for the year (e.g., second examination of the patient out of four examinations of the patient scheduled for the year), and/or an appointment number associated with the medical professional for the day (e.g., second examination a medical professional has out of four examinations the medical professional has scheduled for the day). In some examples, the duration of the appointment 708 may display an amount of time allotted for the patient's examination. Additionally, or alternatively, the duration of the appointment 708 may display an amount of time remaining in a patient examination.

In some examples, the device 702 may be configured to present only a set of throttled recommendation(s) 704, determined to be the most important recommendations to display to medical professional during an examination with a specified patient. The set of throttled recommendations may be generated or determined by remote computing resource(s) 114 using any of the methods described above with respect to FIG. 2. The set of throttled recommendation(s) 704 may be any number of the recommendations, and a number of the recommendation(s) may be determined by the remote computing resource(s) 114 using any of the methods describe above with respect to FIG. 2.

Additionally, or alternatively, the device 702 may be configured to present all of the medical recommendations to a medical professional. For example, the device 702 may be configured to present the recommendation(s) in a manner such that the set of throttled recommendation(s) 704 is emphasized to a user 710. Additionally, or alternatively, additional recommendation(s) not included in the set 712 may be presented such that they are not emphasized or deemphasized to a user 710. Additionally, or alternatively, the remote computing resource(s) 114 may replace any of the recommendations with a new medical recommendation using any of the methods described above with respect to FIG. 2.

CONCLUSION

While the foregoing invention is described with respect to the specific examples, it is to be understood that the scope of the invention is not limited to these specific examples. Since other modifications and changes varied to fit particular operating requirements and environments will be apparent to those skilled in the art, the invention is not considered limited to the example chosen for purposes of disclosure and covers all changes and modifications which do not constitute departures from the true spirit and scope of this invention.

Although the application describes embodiments having specific structural features and/or methodological acts, it is to be understood that the claims are not necessarily limited to the specific features or acts described. Rather, the specific features and acts are merely illustrative some embodiments that fall within the scope of the claims of the application.

What is claimed is:

1. A system comprising:
one or more processors; and
non-transitory computer-readable media storing computer-executable instructions that, when executed by the one or more processors, cause the one or more processors to perform operations comprising:
identifying first data indicating first historical use, by a medical service provider, of an application configured to present medical recommendations associated with a patient;
identifying second data indicating second historical use, by the medical service provider, of the application configured to present medical recommendations associated with the patient;
identifying a first ranking based at least in part on the first data and the second data;
receiving third data indicating a schedule associated with the medical service provider, the schedule including appointments including a first appointment associated with the patient, the first appointment indicating a duration of time scheduled for the first appointment;
generating a machine learning model configured to determine medical recommendations associated with the patient, individual ones of the medical recommendations including at least one of a potential diagnosis, a gap in medical coverage, or a medication recommendation;
generating a training dataset indicating outcomes of the machine learning model when determining medical recommendations associated with the patient, wherein the first ranking and the third data are altered to generate the training dataset formatted as input data to be utilized by the machine learning model;
generating a trained machine learning model based at least in part on training the machine learning model utilizing the training dataset;
determining, based at least in part on inputting the first ranking and the third data into the trained machine learning model, a first set of the medical recommendations to present on a graphical user interface (GUI) during the first appointment;
receiving, from a device associated with the application, location data indicating a current location of the device;
determining that the current location of the device is within a threshold proximity to a residence associated with the patient;
generating, based at least in part on determining that the current location of the device is within the threshold proximity, fourth data representing the GUI including the first set of the medical recommendations;
sending the fourth data to the device at a first time that is prior to the first appointment, the fourth data causing the device to display the GUI including the first set of the medical recommendations at a second time that is during the first appointment;
receiving, via the GUI, input data representing at least an approval or a rejection associated with a first medical recommendation of the first set of the medical recommendations;
determining a second set of the medical recommendations based at least in part on the approval or the rejection associated with the first medical recommendation, the second set of the medical recommendations comprising at least one of:
a subset of the first set of the medical recommendations, wherein the subset is based at least in part on a removal of a second medical recommendation that is associated with the first medical recommendation from the first set of the medical recommendations; or
a third medical recommendation associated with the first medical recommendation, the third medical recommendation being absent from the first set of the medical recommendations;
determining a second ranking associated with the second set of the medical recommendations based at least in part on the approval or the rejection associated with the first medical recommendation and the second data;
sending fifth data to the device at a third time that is after the first appointment begins, the fifth data causing the GUI to display the second set of the medical recommendations according to the second ranking the third time, the third time being subsequent to the second time and prior to an end of the first appointment.

2. The system of claim 1, wherein:
the first data includes at least one of:
an account of a medical professional associated with the medical service provider;
an amount of time that the medical service provider has utilized the application; or
a likelihood that the medical service provider will utilize the medical recommendations;
the second data includes a total number of times that the medical provider or an additional medical provider has utilized the application in association with the account associated with the patient; and
the third data includes at least one of:
a first number of appointments scheduled during a day;
a second number of appointments associated with the patient scheduled during a year; or
an amount of time between the first appointment and a second appointment scheduled after the first appointment.

3. The system of claim 2, the operations further comprising:
determining that the amount of time satisfies a threshold amount of time to present at least the first medical recommendation;
determining the second set of the medical recommendations to present on the GUI during the first appointment based at least in part on the first data, the third data, and the first ranking, wherein the second set includes a greater number of the medical recommendations than the first set; and
wherein the fifth data causes the device to display the GUI including the second set of the medical recommendations during the amount of time between the first appointment and the second appointment.

4. The system of claim 2, the operations further comprising:
determining that the first medical recommendation of the first set of the medical recommendations corresponds to a third medical recommendation of the first set of the medical recommendations;
determining a first priority associated with the first medical recommendation;

determining a second priority associated with the third medical recommendation; and replacing, in the first set of the medical recommendations, the third medical recommendation with a fourth medical recommendation based at least in part on the first medical recommendation corresponding to the third medical recommendation, the first priority being more favorable than the second priority, and the first ranking, wherein the fourth medical recommendation is different from the medical recommendations included in the first set of the medical recommendations.

5. A method comprising:

identifying first data indicating first historical use, by a medical service provider, of an application configured to present medical recommendations associated with a patient;

identifying a first ranking based at least in part on the first data;

receiving second data indicating a schedule associated with the medical service provider, the schedule including appointments including a first appointment associated with the patient, the first appointment indicating a duration of time scheduled for the first appointment;

generating a machine learning model configured to determine medical recommendations associated with the patient, individual ones of the medical recommendations including at least one of a potential diagnosis, a gap in medical coverage, or a medication recommendation;

generating a training dataset indicating outcomes of the machine learning model when determining medical recommendations associated with the patient, wherein the first ranking and the second data are altered to generate the training dataset formatted as input data to be utilized by the machine learning model;

generating a trained machine learning model based at least in part on training the machine learning model utilizing the training dataset;

determining, based at least in part on inputting the first ranking and the second data into the trained machine learning model, a first set of the medical recommendations;

receiving location data indicating a location of a device associated with the application;

generating, based at least in part on determining that the location of the device is within a threshold proximity to a residence associated with the patient, third data representing a graphical user interface (GUI) including the first set of the medical recommendations;

sending the third data to the device at a first time that is prior to an appointment associated with the patient, the third data causing the device to display the GUI including the first set of the medical recommendations during the appointment associated with the patient;

receiving fourth data representing a rejection associated with a first medical recommendation of the first set of the medical recommendations;

determining a second set of the medical recommendations based at least in part on the rejection, the second set of the medical recommendations comprising a subset of the first set of the medical recommendations, wherein the subset is based at least in part on a removal of a second medical recommendation that is associated with the first medical recommendation for the first set of the medical recommendations;

determining a second ranking associated with the second set of the medical recommendations based at least in part on the rejection associated with the first medical recommendation and the first data; and sending fifth data to the device at a third time that is after the appointment begins, the fifth data causing the GUI to display the second set of the medical recommendations according to the second ranking at the third time.

6. The method of claim 5, wherein:

the first data includes:

first historical use of the application by a medical service provider, indicating at least one of:

an account of a medical professional associated with the medical service provider;

an amount of time that the medical service provider has utilized an application configured to present the medical recommendations;

a total number of times that the medical service provider has utilized the application; or a likelihood that the medical service provider will utilize the medical recommendations;

second historical use of the application in association with the patient, indicating a total number of times that the medical service provider or an additional medical service provider has utilized the application in association with the account associated with the patient; and the second data includes at least one of:

a first number of appointments scheduled during a day;

a second number of appointments associated with the patient scheduled during a year; or an amount of time between the appointment and an additional appointment scheduled after the appointment.

7. The method of claim 6, further comprising:

determining that the amount of time satisfies a threshold amount of time;

determining the second set of the medical recommendations based at least in part on the first data, the second data, and the first ranking, wherein the second set includes a greater number of the medical recommendations than the first set; and wherein the fifth data causes the device to display the GUI including the second set of the medical recommendations during the amount of time between the appointment and the additional appointment.

8. The method of claim 5, further comprising:

determining that a first medical recommendation of the first set of the medical recommendations corresponds to a third medical recommendation of the first set of the medical recommendations;

determining a first priority associated with the first medical recommendation;

determining a second priority associated with the third medical recommendation; and replacing, in the first set of the medical recommendations, the third medical recommendation with a fourth medical recommendation based at least in part on the first medical recommendation corresponding to the third medical recommendation, the first priority being more favorable than the second priority, and the first ranking, wherein the fourth medical recommendation is different from the medical recommendations included in the first set of the medical recommendations.

9. The method of claim 5, wherein:
determining the first set of the medical recommendations is based at least in part on a priority associated with the medical recommendations; and
individual ones of the medical recommendations including at least one of a potential diagnosis, a gap in medical coverage, or a medication recommendation.

10. The method of claim 9, further comprising:
receiving, from the medical service provider, an input associated with the first medical recommendation of the first set of the medical recommendations, the input indicating a treatment plan associated with the first medical recommendation;
associating the treatment plan with the at least one of the potential diagnosis, the gap in medical coverage, or the medication recommendation;
determining that the treatment plan corresponds to the second medical recommendation of the first set of the medical recommendations;
associating a lower priority with the second medical recommendation based at least in part on determining that the treatment plan corresponds to the second medical recommendation; and
generating the second set of the medical recommendations, based at least in part on associating the lower priority with the second medical recommendation.

11. The method of claim 9, further comprising:
determining a medical severity associated with the at least one of the potential diagnosis, the gap in medical coverage, or the medication recommendation of the medical recommendations; and
wherein the priority associated with the medical recommendations is based at least in part on the medical severity.

12. The method of claim 5, further comprising:
receiving justifications associated with the medical recommendations; and
wherein the determining the first set of the medical recommendations is based at least in part on the justifications.

13. A system comprising:
one or more processors; and
non-transitory computer-readable media storing computer-executable instructions that, when executed by the one or more processors, cause the one or more processors to perform operations comprising:
identifying first data indicating first historical use, by a medical service provider, of an application configured to present medical recommendations associated with a patient;
identifying a first ranking based at least in part on the first data;
receiving second data indicating a schedule associated with the medical service provider, the schedule including appointments including a first appointment associated with the patient, the first appointment indicating a duration of time scheduled for the first appointment;
generating a machine learning model configured to determine medical recommendations associated with the patient, individual ones of the medical recommendations including at least one of a potential diagnosis, a gap in medical coverage, or a medication recommendation;
generating a training dataset indicating outcomes of the machine learning model when determining medical recommendations associated with the patient, wherein the first ranking and the second data are altered to generate the training dataset formatted as input data to be utilized by the machine learning model;
generating a trained machine learning model based at least in part on training the machine learning model utilizing the training dataset;
determining, based at least in part on inputting the first ranking and the second data into the trained machine learning model, a first set of the medical recommendations;
receiving location data indicating a location of a device associated with the application;
generating, based at least in part on determining that the location of the device is within a threshold proximity to a residence associated with the patient, third data representing a user interface including the first set of the medical recommendations;
sending the third data to the device at a first time that is prior to an appointment associated with the patient, the third data causing the device to display the user interface including the first set of the medical recommendations at a second time that is during the appointment associated with the patient;
receiving fourth data representing an approval associated with a first medical recommendation of the first set of the medical recommendations;
determining a second set of the medical recommendations based at least in part on the approval, the second set of the medical recommendations comprising a second medical recommendation associated with the first medical recommendation, the second medical recommendation being absent from the first set of the medical recommendations;
determining a second ranking associated with the second set of the medical recommendations based at least in part on the approval associated with the first medical recommendation and the first data; and
sending fifth data to the device at a third time that is after the appointment begins, the fifth data causing the user interface to display the second set of the medical recommendations according to the second ranking at the third time.

14. The system of claim 13, wherein:
the first data includes:
first historical use of the application by a medical service provider, indicating at least one of:
an account of a medical professional associated with the medical service provider;
an amount of time that the medical service provider has utilized an application configured to present the medical recommendations;
a total number of times that the medical service provider has utilized the application; or
a likelihood that the medical service provider will utilize the medical recommendations;
second historical use of the application in association with the patient, indicating a total number of times that the medical service provider or an additional medical service provider has utilized the application in association with the account associated with the patient; and
the second data includes at least one of:
a first number of appointments scheduled during a day;
a second number of appointments associated with the patient scheduled during a year; or an amount of time between the appointment and an additional appointment scheduled after the appointment.

15. The system of claim 14, the operations further comprising:
determining that the amount of time satisfies a threshold amount of time;
determining the second set of the medical recommendations based at least in part on the first data, the second data, and the first ranking, wherein the second set includes a greater number of the medical recommendations than the first set; and
wherein the fifth data causes the device to display the user interface including the second set of the medical recommendations during the amount of time between the appointment and the additional appointment.

16. The system of claim 13, the operations further comprising:
determining that a first medical recommendation of the first set of the medical recommendations corresponds to a third medical recommendation of the first set of the medical recommendations;
determining a first priority associated with the first medical recommendation;
determining a second priority associated with the third medical recommendation; and
replacing, in the first set of medical recommendations, the third medical recommendation with a fourth medical recommendation based at least in part on the first medical recommendation corresponding to the third medical recommendation, the first priority being more favorable than the second priority, and the first ranking, wherein the fourth medical recommendation is different from the medical recommendations included in the first set of the medical recommendations.

17. The system of claim 13, wherein:
determining the first set of the medical recommendations is based at least in part on a priority associated with the medical recommendations; and
individual ones of the medical recommendations including at least one of a potential diagnosis, a gap in medical coverage, or a medication recommendation.

18. The system of claim 17, the operations further comprising:
receiving, from the medical service provider, an input associated with the first medical recommendation of the first set of the medical recommendations, the input indicating a treatment plan associated with the first medical recommendation;
associating the treatment plan with the at least one of the potential diagnosis, the gap in medical coverage, or the medication recommendation;
determining that the treatment plan corresponds to the second medical recommendation of the first set of the medical recommendations;
associating a lower priority with the second medical recommendation based at least in part on determining that the treatment plan corresponds to the second medical recommendation; and
generating the second set of the medical recommendations, based at least in part on associating the lower priority with the second medical recommendation.

19. The system of claim 17, the operations further comprising:
determining a medical severity associated with the at least one of the potential diagnosis, the gap in medical coverage, or the medication recommendation of the medical recommendations; and
wherein the priority associated with the medical recommendations is based at least in part on the medical severity.

20. The system of claim 13, the operations further comprising:
receiving justifications associated with the medical recommendations; and
wherein the determining the first set of the medical recommendations is based at least in part on the justifications.

* * * * *